(12) United States Patent
Shin et al.

(10) Patent No.: US 7,196,318 B2
(45) Date of Patent: Mar. 27, 2007

(54) FIBER-OPTIC SENSING SYSTEM

(75) Inventors: Chow-Shing Shin, 5th Fl., No. 50, Lane 21, Sec. 4, Hsinhai Rd., Taipei City 116 (TW); Kin-Man Yip, 12th Fl., No. 10, Alley No. 4, Lane 284, Jung Jeng Road, Hsintien, Taipei County (TW); Chia-Chin Chiang, Keelung (TW)

(73) Assignees: Kin-Man Yip, Chung-Ho (TW); Chow-Shing Shin, Chung-Ho (TW)

( * ) Notice: Subject to any disclaimer, the term of this patent is extended or adjusted under 35 U.S.C. 154(b) by 0 days.

(21) Appl. No.: 10/892,267

(22) Filed: Jul. 16, 2004

(65) Prior Publication Data

US 2006/0011820 A1  Jan. 19, 2006

(51) Int. Cl.
*G01J 5/08* (2006.01)

(52) U.S. Cl. .................. 250/227.16; 250/227.14; 385/13; 73/705

(58) Field of Classification Search ........... 250/227.14–227.16; 385/12, 13; 73/705, 708; 600/480, 488
See application file for complete search history.

(56) References Cited

U.S. PATENT DOCUMENTS

| | | | |
|---|---|---|---|
| 4,691,708 A | 9/1987 | Kane | 600/480 |
| 4,711,246 A | 12/1987 | Alderson | 600/480 |
| 4,924,870 A | 5/1990 | Wlodarczyk et al. | 600/480 |
| 5,107,847 A | 4/1992 | Knute et al. | 600/488 |
| 5,196,694 A * | 3/1993 | Berthold et al. | 250/227.16 |
| 5,275,053 A | 1/1994 | Wlodarczyk et al. | 73/705 |
| 5,385,053 A | 1/1995 | Wlodarczyk et al. | 73/705 |
| 5,386,729 A * | 2/1995 | Reed et al. | 73/705 |
| 5,394,488 A * | 2/1995 | Fernald et al. | 385/13 |
| 5,422,478 A | 6/1995 | Wlodarczyk et al. | 250/227.21 |
| 5,841,131 A * | 11/1998 | Schroeder et al. | 250/227.17 |

(Continued)

OTHER PUBLICATIONS

Pollintine P, Przybyla AS, Dolan P, Adams MA. Neural arch load-bearing in old and degenerated spines. *J Biomech* 2004;37:197-204.

(Continued)

*Primary Examiner*—Thanh X. Luu
*Assistant Examiner*—Stephen Yam
(74) *Attorney, Agent, or Firm*—Thomas Kayden, Horstemeyer & Risley LLP

(57) ABSTRACT

The invention provides a fiber-optic sensing system, utilizing a fiber-grating-based sensor, for a physical parameter, e.g., a pressure or a temperature. Different kinds of fiber-grating-based sensors may be used for this purpose but in-fiber gratings such as Fiber Bragg Grating, Long Period Grating and Surface Corrugated Long Period Fiber Grating are particularly suitable. Due to the small size of the optical fiber and the fact that same fiber acts as the sensing element as well as the signal conducting medium, it is possible to install the sensor in a small diameter needle which is commonly used for medical diagnosis and treatment. As a result, when the fiber-optic sensing system of the invention is used for in-vivo measurement of a biological parameter, such a sensing needle can be used for different in-vivo pressure or temperature sensing applications without causing too much harm and discomfort to the subject tested.

15 Claims, 10 Drawing Sheets

U.S. PATENT DOCUMENTS

| | | | |
|---|---|---|---|
| 6,016,702 A * | 1/2000 | Maron | 73/705 |
| 6,125,216 A * | 9/2000 | Haran et al. | 385/12 |
| 6,218,661 B1 * | 4/2001 | Schroeder et al. | 250/227.14 |
| 6,276,215 B1 * | 8/2001 | Berg | 73/800 |
| 6,278,811 B1 * | 8/2001 | Hay et al. | 385/13 |
| 6,563,970 B1 * | 5/2003 | Bohnert et al. | 385/13 |
| 6,740,866 B1 * | 5/2004 | Bohnert et al. | 250/227.14 |
| 6,898,339 B2 * | 5/2005 | Shah et al. | 385/13 |

OTHER PUBLICATIONS

Sato K, Kikuchi S, Yonezawa T. In Vivo intradiscal pressure measurement in healthy individuals and in patients with ongoing back problems. Spine1999;24:2468-74.

Wilke HJ, Neef P, Caimi M, Hoogland T, Claes LE. New in-vivo measurements of pressures in the intervertebral disc in daily life. Spine 1999;24:755-62.

McNally DS, Shackleford IM, Goodship AE, Mulholland RC. In vivo stress measurement can predict pain on discography. Spine 1996;21(22):2580-7.

* cited by examiner

FIBER-OPTIC SENSING SYSTEM

BACKGROUND OF THE INVENTION

1. Field of the Invention

This invention relates to the sensing of physical parameter, such as pressure or temperature, using in-fiber sensors, e.g., short period fiber Bragg grating, long period fiber grating or surface corrugated long period fiber grating. Since signal sensing and signal transfer can both occur in the same fiber, it is possible to derive miniature pressure or temperature sensing systems or transducers for use in medical diagnoses in the areas of intradiscal, intracranial, intramuscular, intra-articular, ventricular pressure or temperature monitoring with minimum invasiveness. For example, for intra-articular pressure measurement, the small size of the needle means that the pressure of small joint cavities like the temporo-mandibular joint, the facet joints of the vertebral column, the carpal joints of the wrist and the tarsal joints of the midfoot region can also be assessed by means of this device. With respect to the technology background of the invention, please refer to the following references:

[1] Pollintine P, Przybyla A S, Dolan P, Adams M A. Neural arch load-bearing in old and degenerated spines. *J Biomech* 2004;37:197–204.;
[2] Sato K, Kikuchi S, Yonezawa T. In Vivo intradiscal pressure measurement in healthy individuals and in patients with ongoing back problems. Spine 1999;24: 2468–74;
[3] Wilke H J, Neef P, Caimi M, Hoogland T, Claes L E. New in-vivo measurements of pressures in the intervertebral disc in daily life. Spine 1999;24:755–62;
[4] McNally D S, Shackleford I M, Goodship A E, Mulholland R C. In vivo stress measurement can predict pain on discography. Spine 1996;21(22):2580–7;
[5] Kane; James, "Optical pressure sensor for measuring blood pressure", U.S. Pat. No. 4,691,708;
[6] Wallace L. Knute, Wilber H. Bailey, "Fiber-optic transducer apparatus", U.S. Pat. No. 5,107,847;
[7] Alderson; Richard, "Fiber optic coupled pressure transducer using single fiber and method of fabrication", U.S. Pat. No. 4,711,246;
[8] U.S. Pat. No. 4,924,870;
[9] U.S. Pat. No. 5,275,053;
[10] U.S. Pat. No. 5,385,053; and
[11] U.S. Pat. No. 5,422,478.

2. Description of the Prior Art

Pressure measurement is important in engineering, medical diagnosis and research and development in many fields. Technology used in conventional pressure measurement may be broadly differentiated into mechanical, electrical and fiber-optic categories. A diaphragm that can deform under the application of pressure is normally employed as the primary transducer for pressure. The deformation of the diaphragm is converted into the movement of a dial pointer through suitable mechanisms in the mechanical pressure gage. The use of purely mechanical components makes this type of gages very bulky. In the electrical category, resistive strain gages are normally employed to convert the diaphragm deformation into electrical signals. Although this type of pressure transducer can be made much smaller than the mechanical ones, the size of the strain gages and the need to lead out a number of wires for electrical excitation and signal measurement make it difficult to reduce their size to below the millimeter level. Typical small-sized pressure probe of this category used for in-vivo medical measurement has a diameter from 1.5 to 3 mm, please refer to references [1] to [4]. At these sizes, the implantation of the pressure transducer to make in-vivo measurement is a rather invasive procedure and could mean much discomfort to the subject concerned. This type of transducer is also susceptible to electromagnetic interference and measurement accuracy may be affected if there are other medical instruments nearby.

Referring to references [5], [6] and [7], the typical fiber-optic pressure transducer system comprises two sets of optical fibers. One set of fibers transmits a light beam to shine on the deformable diaphragm and the other set of fibers returns a modulated light beam reflected from the diaphragm. It is also possible to use a single optical fiber for the two-way light traffic, please refer to reference [7]. Pressure variation will deform the diaphragm, thereby varying the proximity of the diaphragm to the fiber ends, thus modulating the intensity of the reflected light. By measuring the reflected light intensity using a photo-sensor, the pressure can be deduced. Good alignment of the fibers and the reflecting surface of the diaphragm is needed and high precision manufacturing process make this kind of sensor expensive to produce. This type of transducers have not been entirely satisfactory as the intensity of light transmitted in an optical fiber can be reduced by bending of any part of the fiber, movement of the pressure probe and a faulty connector. Moreover, temperature fluctuation may also affect the accuracy of the measurement. In fact, there are a number of inventions made to combat these problems, please refer to references [8], [9], [10] and [11], but this often means packing some more optical fibers into the transducer for reference purposes.

SUMMARY OF THE INVENTION

In view of the limitation of related conventional arts, one objective of this invention is to provide a low cost yet simple and robust fiber-optic sensing system for measurement of pressure or temperature, especially for in-vivo pressure or temperature, whose measurement accuracy is independent of the bending of the fiber and temperature fluctuations. Pressure or temperature measurement at multiple sites can also be achieved by having a number of fiber-grating-based sensors along the optical fiber. Simultaneous temperature may also be made in the vicinity of the pressure measuring point.

Another objective of this present invention is to provide a miniature pressure or temperature transducer suitable for in-vivo measurement with minimal invasiveness. The miniature transducer will also be useful for pressure measurement in engineering structures and compartments too small to house a conventional sensor. The transducer can be used in adverse environment that involves magnetic field, electromagnetic interference, and ionizing radiation.

As aforementioned, this present invention provides a fiber-optic pressure transducer, comprising: an outer sheath with closed distal end, one or more windows on the sheath, diaphragms covering and sealing each of the windows, an optical fiber running from the distal end of the sheath to a data processing and read-out instrument, and a designated number of in-fiber sensing elements along the length of the optical fiber. These sensing element can be fiber Bragg grating, long period grating or periodic surface corrugation that exhibits long period grating effect under deformation. When the flexible diaphragm deform under pressure, the attached in-fiber sensor will be deformed as well, modulating the wavelength of the reflected and/or transmitted light. It should be pointed out that with the current design, in addition to fluid pressure, pressure exerted by soft tissue such as muscle or tissue between vertebrate discs can also be monitored.

The present invention also provides a fiber-optic pressure transducer, comprising: an outer sheath with closed distal end, one or more windows on the sheath, an optical fiber fixed at and running from the distal end of the sheath to a data processing and read-out instrument and a flexible diaphragm downstream of the windows that fix the fiber to the sheath. An in-fiber sensing elements along the length of the optical fiber between the fixed distal end and the diaphragm is used to sense the fluid pressure when the sheath is put into a fluid environment. This sensor will not be able to monitor pressure from soft tissue or fluid that is too viscous to pass into the interior of the sheath through the windows.

By using optical fiber as the sensing and signal conducting element, the overall size of the sensor can be greatly reduced. Standard glass optical fiber has an outer diameter of 125 μm. Smaller diameter fibers are available commercially and it can also be achieved by etching standard fibers. The size of the sheath needs only be slightly (say 50 μm) larger than the fiber although larger sheath can also be used if the other considerations call for it. For in-vivo applications, by integrating the diaphragm/fiber sensor assembly with the spinal needle or other needles, the resulting instrument is robust enough to be deployed by direct insertion to the organ concerned without using an additional catheter. The insertion of such small needle into the body will constitute minimum invasiveness and discomfort.

By employing fiber gratings as sensor, the parameter modulated by the measurand is coded in the wavelength and so intensity fluctuation of the source or random losses caused by bending will not affect the accuracy of measurement. Temperature induced drift in the measurement can be compensated by an independent grating in the same fiber that is fixed to the sheath, exposed to the same temperature but not to the pressure. This additional grating also enabled the local temperature to be monitored alongside with the pressure.

The advantage and spirit of the invention may be understood by the following recitations together with the appended drawings.

BRIEF DESCRIPTION OF THE APPENDED DRAWINGS

FIG. 1A is an outside perspective view of a sheath 12 and an optical fiber 16, disposed in the sheath 12, of a fiber-optic sensing system 1 according to a preferred embodiment of the invention.

DETAILED DESCRIPTION OF THE INVENTION

Figure 1A:
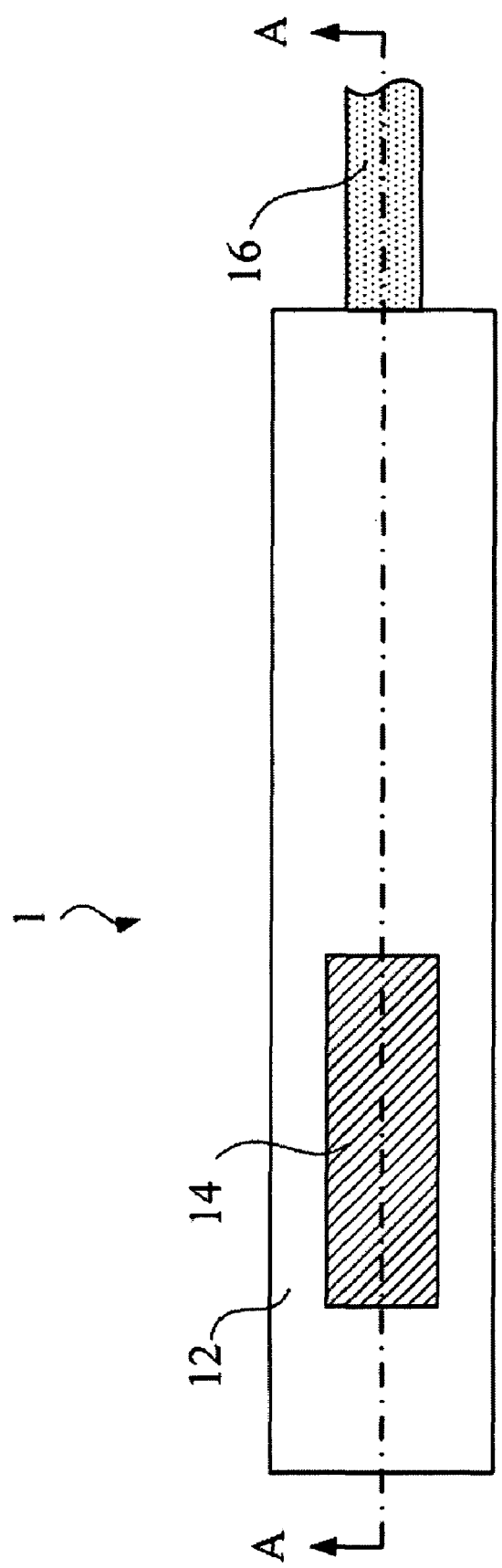
FIG. 1B is a cross section view of the sheath 12 and the optical fiber 16 of FIG. 1A along the A—A line.

A description will now be given of the preferred embodiments of the present invention with reference to the drawings.

In the drawings, the same numeral notation refers to the same element. The drawings and the following detailed descriptions show specific embodiments of the invention. In the preferred embodiment, polymeric adhesive was employed to manufacture the flexible diaphragm and spinal needle was employed as the sheath. Numerous specific details including materials, dimensions, and products are provided to illustrate the invention and to provide a more thorough understanding of the invention. However, it will be obvious to one skilled in the art that the present invention may be practiced using other materials for the sheath and flexible diaphragm and without these specific details.

FIG. 1A is an outside perspective view of a needle 12 and an optical fiber 16, disposed in the needle 12, of a fiber-optic sensing system 1 according to a preferred embodiment of the invention.

Figure 1B:
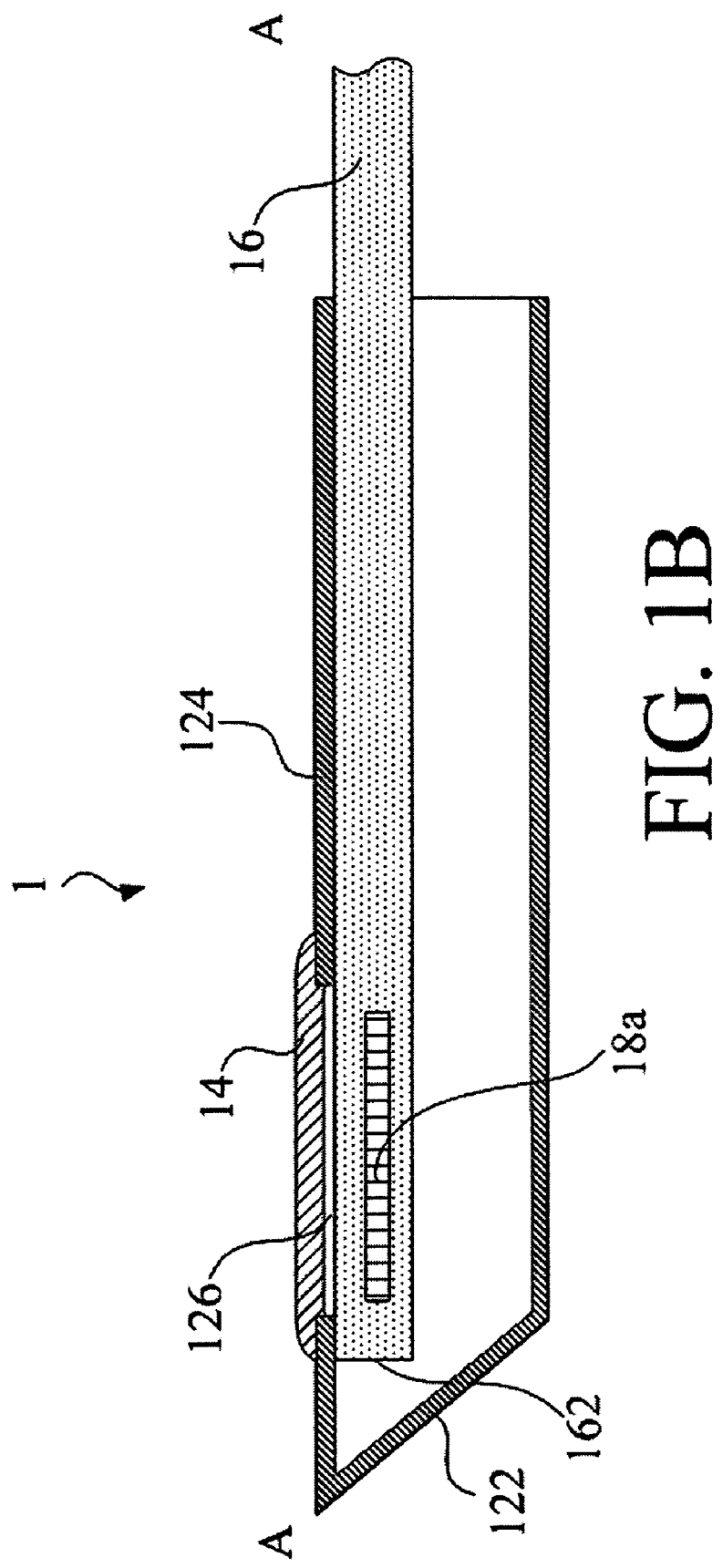

Referring to FIGS. 1A and 1B, the basic structure of the fiber-optic sensing system 1 according to a preferred embodiment of the invention is schematically illustrated. FIG. 1A is a sectional outside perspective view of the fiber-optic sensing system 1. In FIG. 1A, the essentials of the fiber-optic system 1 including a sheath 12 and an optical fiber 16, disposed in the sheath 12, are shown. In this case, the outer sheath 12 is a spinal needle. FIG. 1B is a cross section view of the sheath 12 and the optical fiber 16 of FIG. 1A along A—A line.

As shown in FIG.1B, the sheath 12 has a sealed tip 122, a main body 124 and a formed-through opening 126 formed on the main body 124 and sealed with a diaphragm 14. In this case, an original opening at distal end (needle tip) 122 is sealed with a polymeric adhesive. Also in this case, the opening 126 is machined near the needle tip and is sealed by a flexible polymeric diaphragm 14.

The optical fiber 16 has a distal end 162 and a head end (not shown). The optical fiber 16 thereon includes a fiber-grating-based sensor 18a. In this case, the fiber-grating-based sensor 18a is a fiber Bragg grating (FBG). The optical fiber 16 with the FBG 18a is inserted into the interior of the needle 12. The portion of the optical fiber 16 with the FBG 18a written to the core of the optical fiber 16 is stuck to the inside surface of the flexible diaphragm 14.

The fiber-optic sensing system 1 also includes an optical device and a signal processing device (not shown). The optical device functions emitting a sensing light signal into the second end of the optical fiber 16 and receiving a first reflected light signal resulting from the sensing light signal reflected by the fiber-grating-based sensor 18a. When the needle 12 is inserted into a region, for example, a fluid medium or soft tissue, where a physical parameter needs to be measured, the region affects the fiber-grating sensor 18*a* through the diaphragm 14 to induce a variation on the first reflected light signal. The signal processing device is coupled to the optical device, and functions interpreting the variation on the first reflected light signal into the physical parameter.

Taking pressure as example, pressure in the region will cause a deformation of the diaphragm 14. The FBG 18*a* will be deformed as well and the characteristic Bragg wavelength will be shifted away from its initial position. The amount of shift is proportional to the pressure acting on the diaphragm 14. By measuring the shift in the reflected Bragg wavelength using a suitable signal processing device, the pressure can be deduced.

Figure 2:
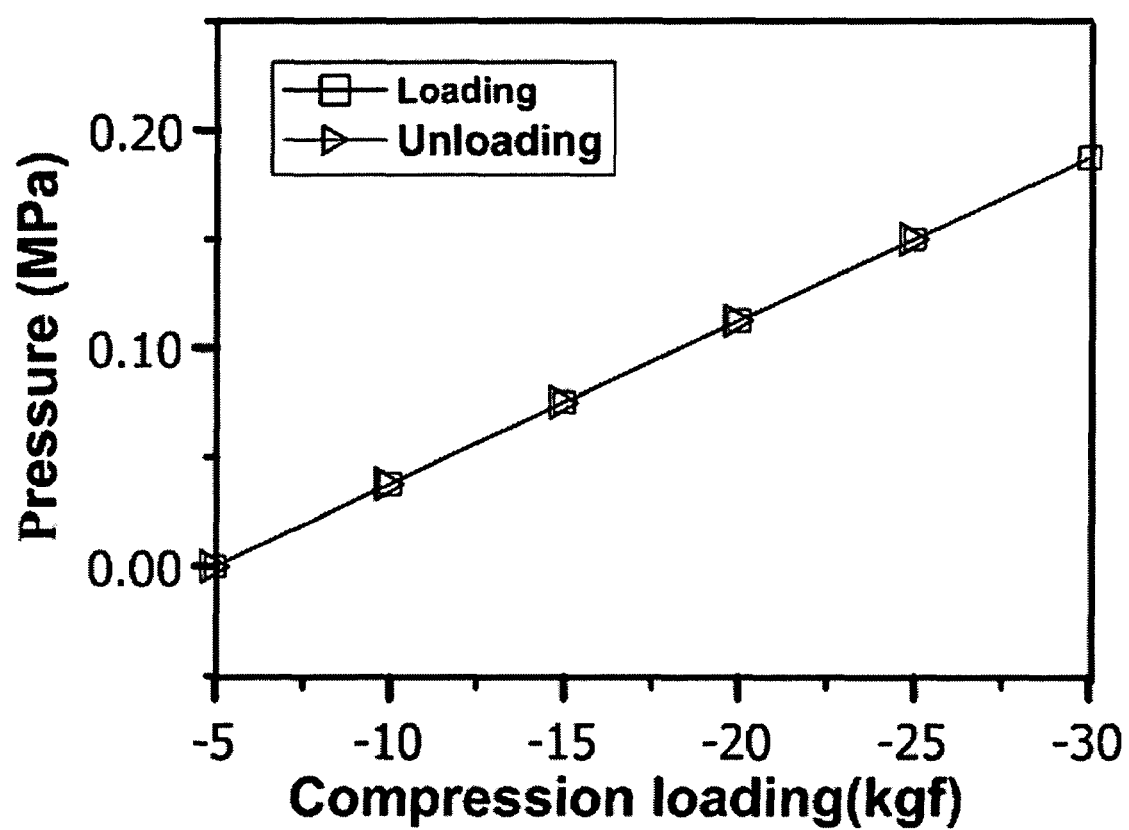
FIG. 2 shows the measured variation in pressure inside the space between two vertebral discs using an embodiment of FIGS. 1A and 1B when the vertebrate segment is subjected to different axial loading.

FIG. 2 shows the variation in pressure measured when a pressure transducer was inserted inside the space between two vertebral discs and the vertebrate segment is subjected to different axial loading. The pressure transducer was obtained by employing the embodiment illustrated in FIGS. 1A and 1B using a 26-G (0.45 mm outer diameter) spinal needle as the outer sheath.

Figure 3:
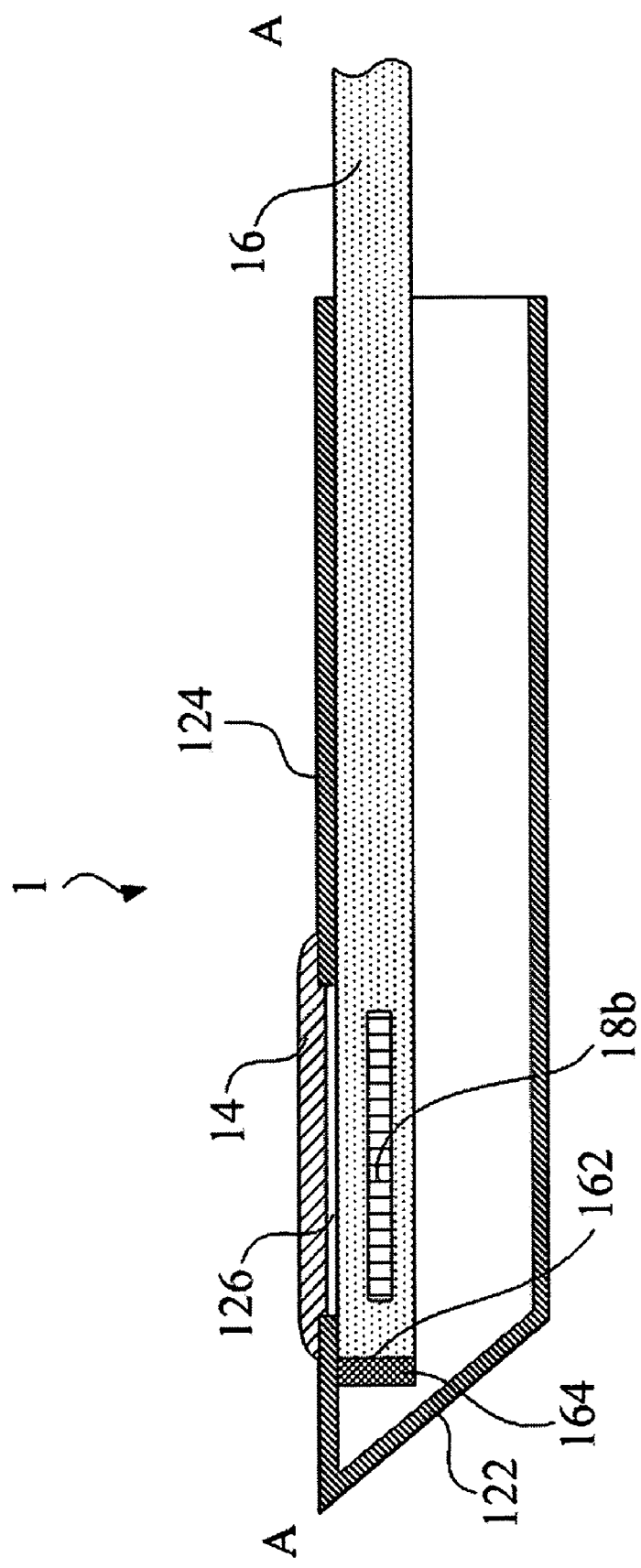
FIG. 3 is schematic drawing showing another embodiment of the invention using a long period grating as the fiber-grating-based sensor.

Besides using a short period fiber Bragg grating, long period grating (LPG) can also be used as the fiber-grating-based sensor, e.g., long period fiber grating or surface corrugated long period fiber grating. FIG. 3 shows another embodiment using the LPG as the fiber-grating-based sensor 18*b*. The LPG 18*b* will attenuate a characteristic spectrum when a broad spectrum light is passed through it. This characteristic spectrum will shift with strain applied to the LPG 18*b*. However, such a characteristic attenuation spectrum is only evident from the transmitted light. To allow this spectrum to be measured at the proximal end, a mirror coating 164 is plated at the distal end 162 of the optical fiber 16 to reflect the transmitted spectrum back. This is illustrated in the embodiment in FIG. 3.

Figure 4:
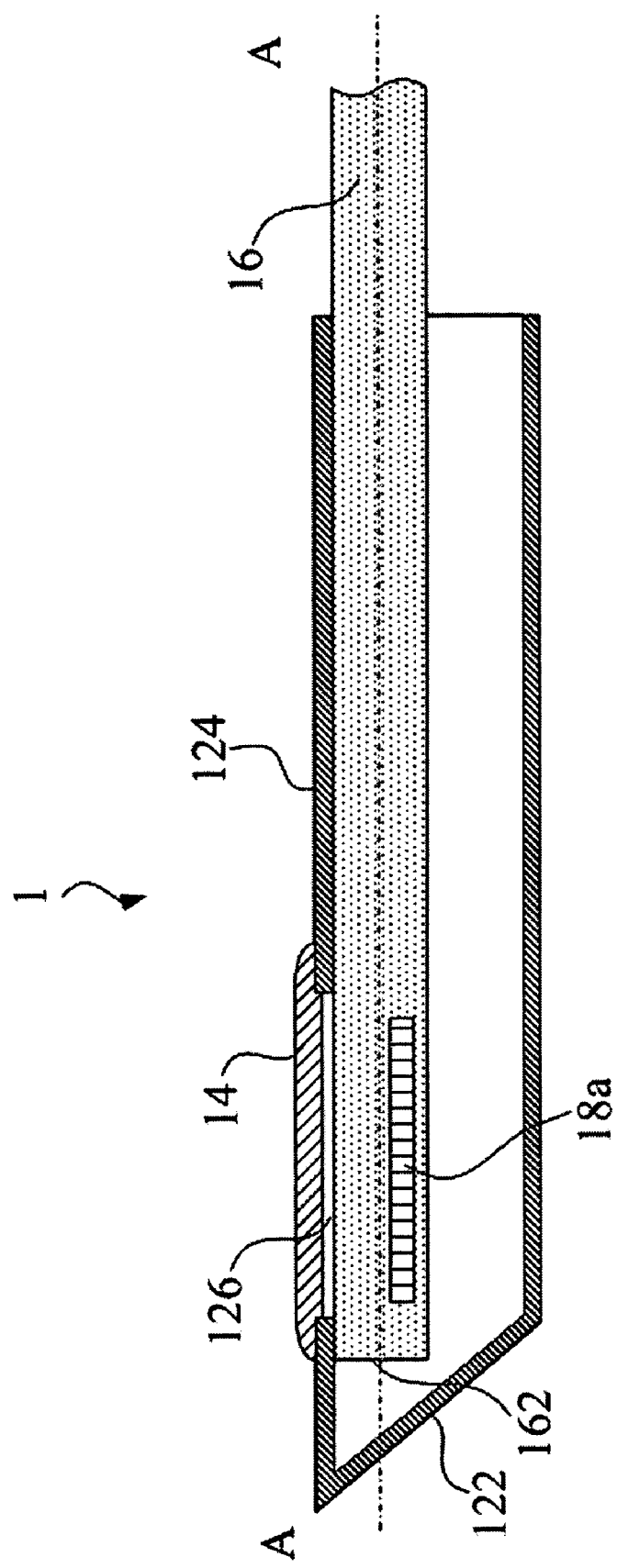
FIG. 4 shows an improvement on the basic structure in FIG. 1B to obtain a better sensitivity by moving the fiber core sensor farther away from the flexible diaphragm.

Since the flexible diaphragm 14 as well as the optical fiber 16 deform by bending, the induced strain in the in-fiber sensor (the fiber-grating-based sensor) 18*a* can be amplified by moving the sensor region further away from the neutral axis (i.e. the axis without extension or contraction under bending). Since the in-fiber sensor 18*a* essentially situated at the core of the optical fiber 16, the above requirement can be achieved by moving the fiber core as far from the flexible diaphragm 14 as possible. FIG. 4 shows yet another embodiment that employs an optical fiber 16 with off-centered core to achieve this purpose. Such an off-centered core may be achieved during the manufacturing of the optical fiber 16. It can also be obtained by selective etching of the cladding on a standard fiber.

Figure 5:
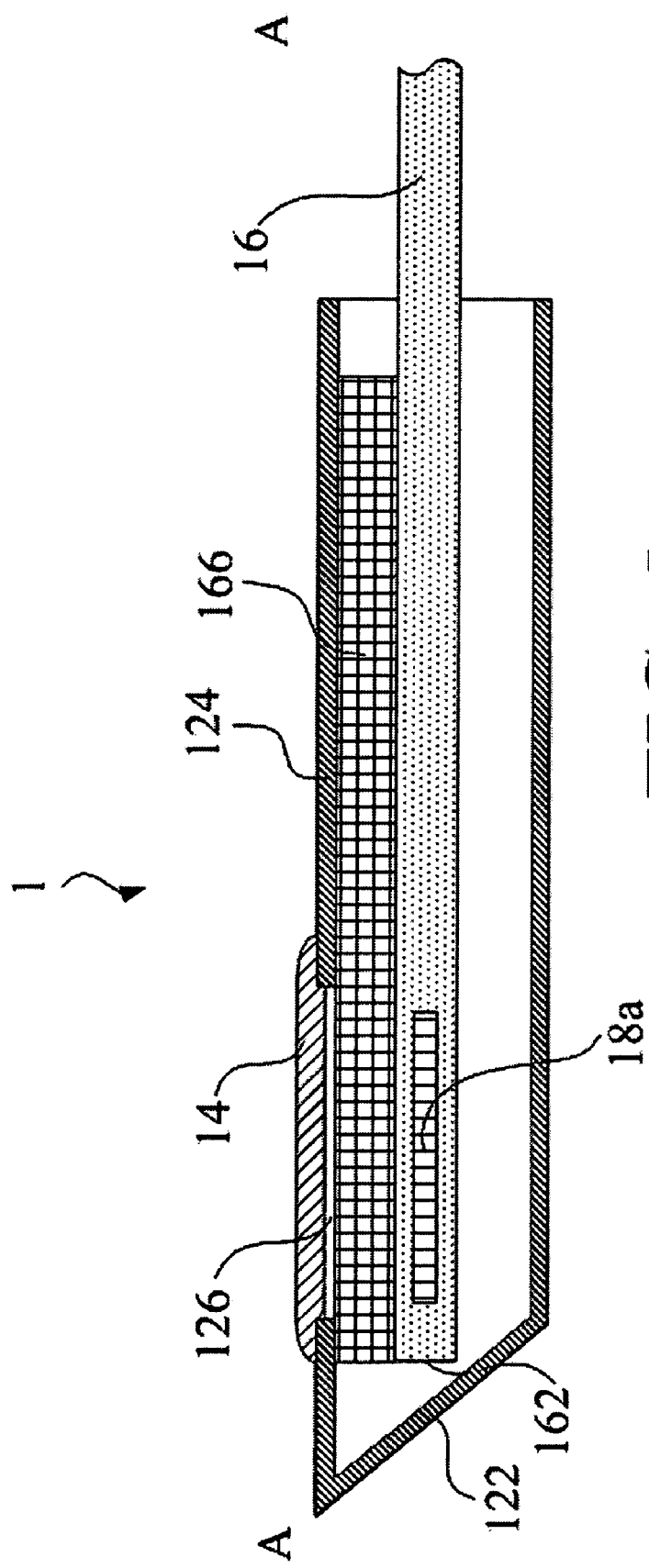
FIG. 5 shows another way to improve sensitivity by adding a low stiffness fiber between the diaphragm and the optical fiber in FIG. 1B.

FIG. 5 shows yet another embodiment to improve sensitivity by moving the core of the optical fiber 16 as far from the flexible diaphragm 14 as possible. It is achieved by bonding a low stiffness fiber 166 between the diaphragm 14 and the optical fiber 16. The stiffness of the additional fiber 166 is chosen to be low so as keep the flexural rigidity of the whole diaphragm/fibers structure low to ensure a higher strain at the fiber core.

Figure 6:
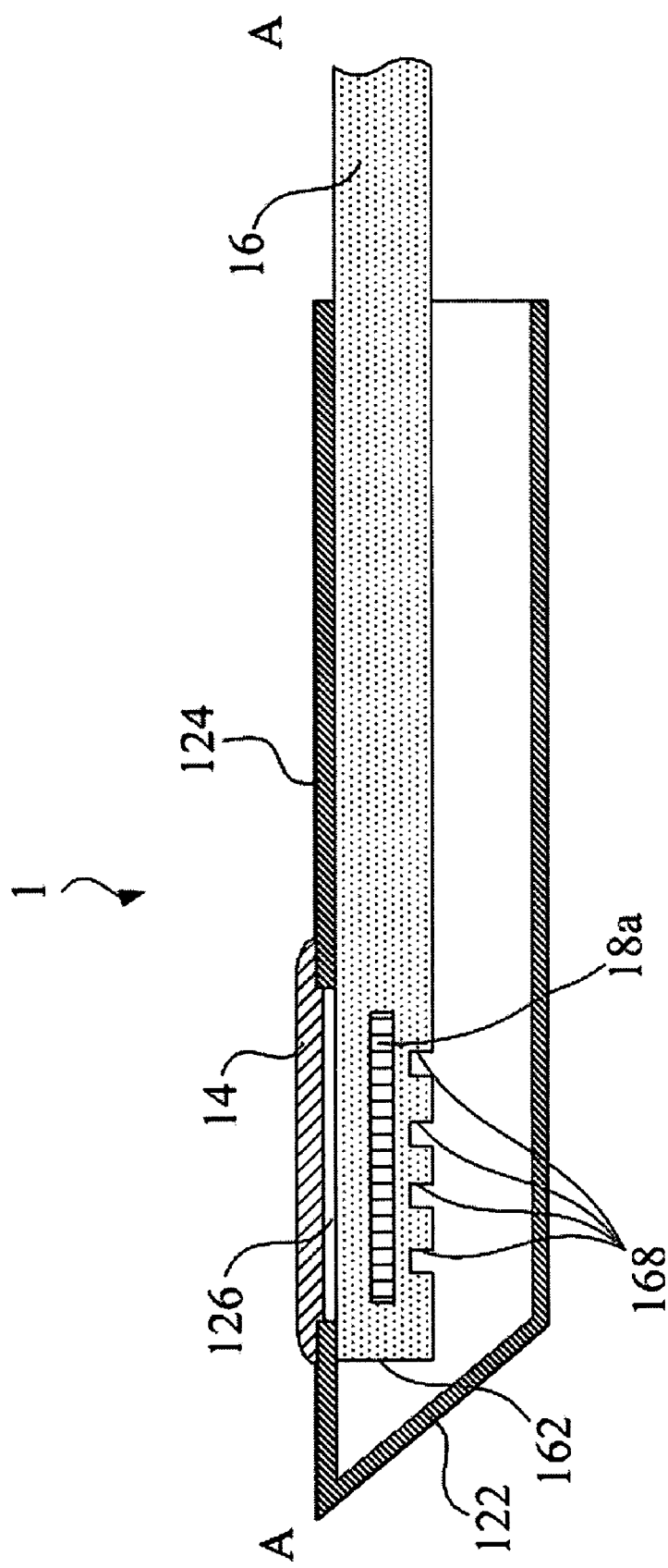
FIG. 6 shows yet another way to increase sensitivity by introducing some notches to the optical fiber in FIG. 1B to induce strain concentration effect.

FIG. 6 shows yet another embodiment to increase the pressure sensitivity by introducing some notches 168 in the cladding of the optical fiber 16 in the vicinity of the in-fiber sensor 18*a*. These notches 168 will induce strain concentration and amplify the strain at the sensor region.

For person skilled in the art, there will be other similar ways to increase the strain and thus the sensitivity of the pressure sensor. For clarity of explanation, a separate technique is employed in each of the above embodiments to increase the sensitivity of the pressure sensor. There is no reason that the different techniques cannot be combined together and applied to the same transducer to obtain the maximum increase in sensitivity. Moreover, in the above embodiments, only one opening and one sensor have been employed. In practice, more openings with multiple in-fiber sensors in the same or multiple optical fibers may be employed to allow the pressure or temperature at multiple sites to be measured.

Figure 7:
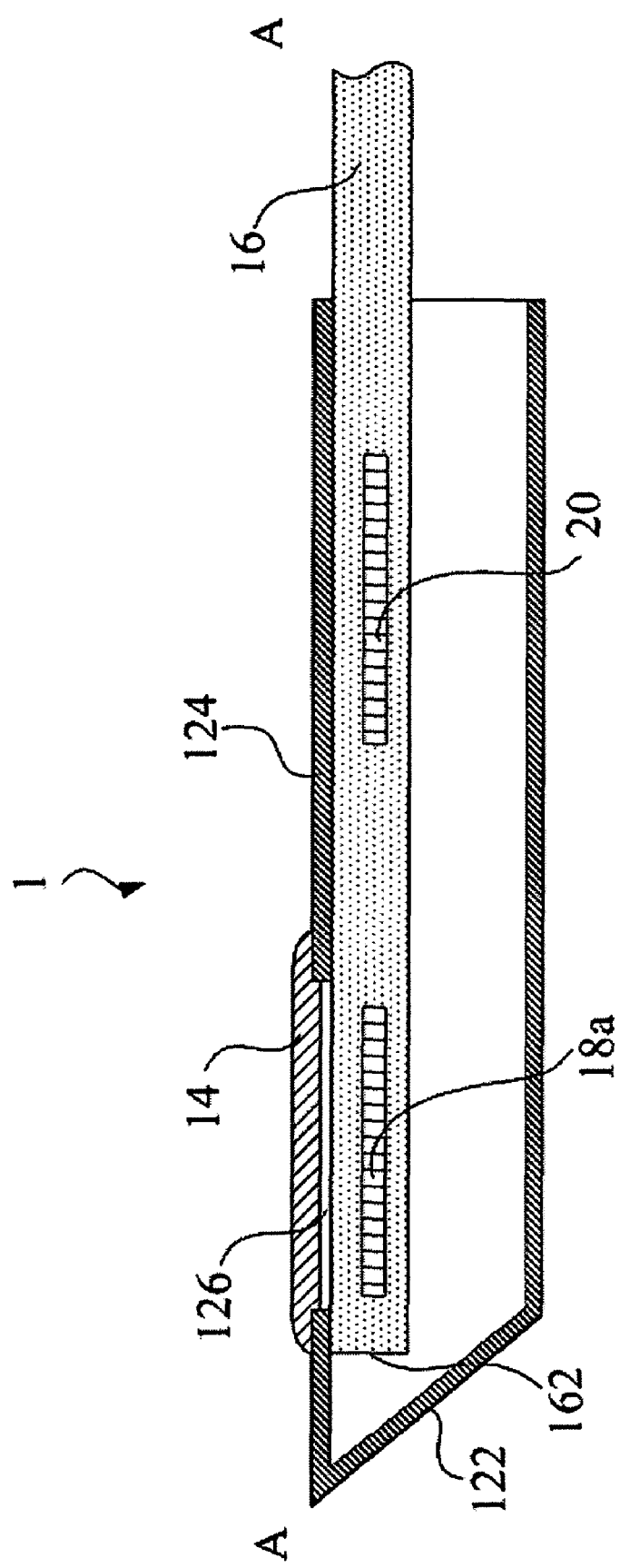
FIG. 7 shows additional fiber-grating-based sensor fixed to the sheath for monitoring the local temperature as well as providing temperature drift correction to the original fiber-grating-based sensor as pressure sensor.

It is well known that fiber-grating-based sensor is sensitive to strain as well as temperature. If temperature fluctuation occurs during measurement, the resulting change in the characteristic spectra will be the combined effect of temperature and pressure variations. FIG. 7 shows an embodiment that may be used to compensate for the temperature induced drift in the characteristic spectra. An additional fiber-grating-based sensor 20 in the optical fiber 16 in the vicinity of the original fiber-grating-based sensor 18*a* underneath the diaphragm 14 is employed. This additional fiber-grating-based sensor 20 is fixed to the sheath 12 and so is isolated from the pressure of the surrounding environment (the region) such that the physical parameter is shielded by the sheath 12 and will not affect the additional fiber-grating-based sensor 20. However, another physical parameters, such as temperature, that cannot be shielded by the sheath 12 will still affect the additional fiber-grating-based sensor 20. Thus variation in the local temperature will cause shift in the characteristic spectrum of the additional fiber-grating-based sensor 20. This enables the local temperature to be monitored. The latter can be used both as additional information as well as to provide temperature drift correction to the pressure sensor (the original fiber-grating-based sensor) 18*a*.

Figure 8A:
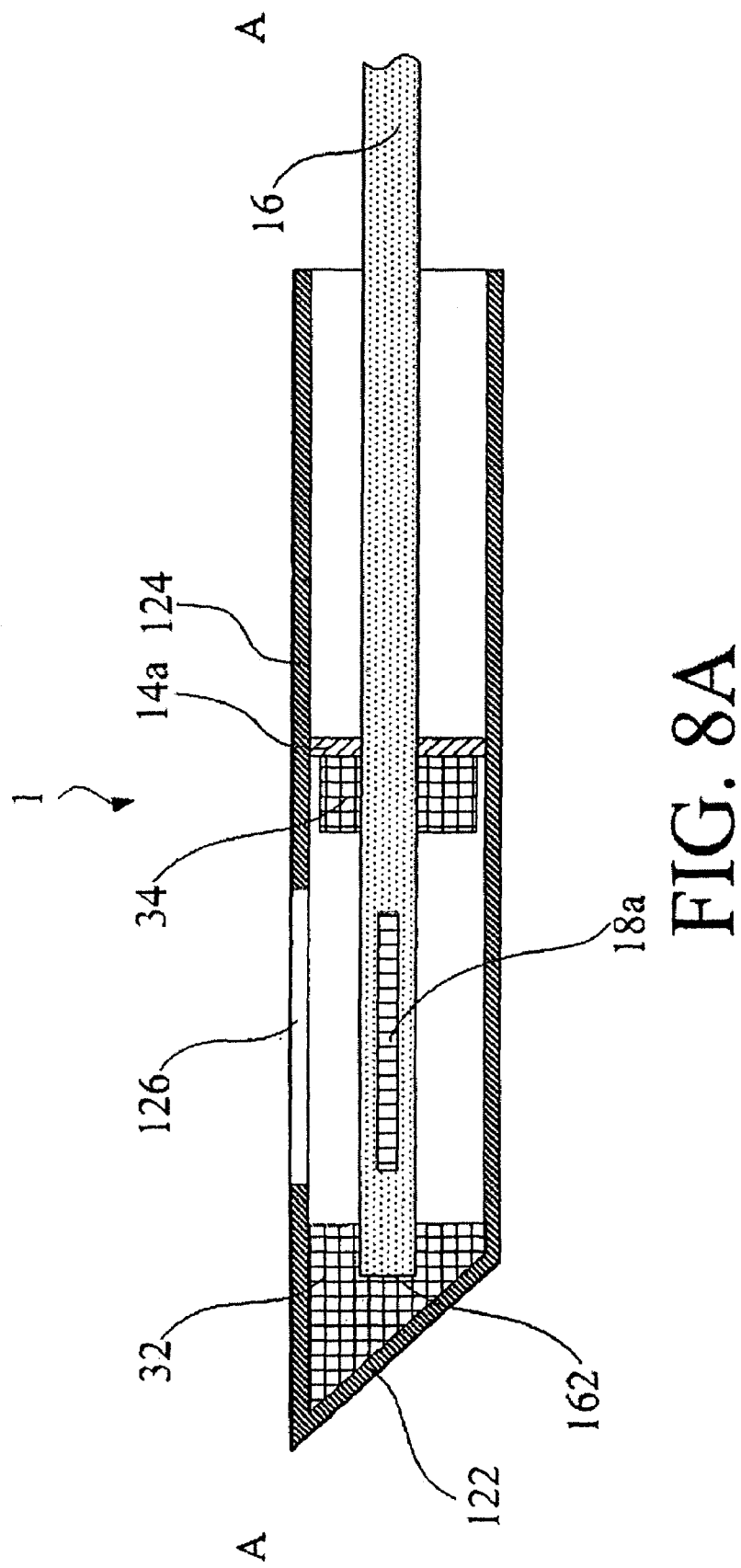
FIG. 8A shows a different layout of the fiber-grating-based sensor in FIG. 1B as pressure sensor wherein the opening is not sealed.

FIG. 8A shows yet another embodiment of the fiber-grating-based sensor 18*a* that uses a slightly different layout as the above embodiments. In this embodiment, the opening 126 is not sealed so that fluid under pressure may flow into the distal part of the sheath 12. A flexible diaphragm 14*a* is situated inside the sheath downstream of the opening 126 to isolate any fluid from going into the proximal end of the sheath 12. The optical fiber 16 is fixed at the distal end 162 using an adhesive 32 upstream of the opening 126. The diameter of the optical fiber 16 near the diaphragm 14*a* is enlarged by attaching additional material (enlarged section) 34 such as polymeric adhesive to the optical fiber 16. The enlargement is made as large as the inside diameter of the sheath 12 can accommodate but still allows smooth axial motion should the optical fiber 16 extend under pressure. This enlarged section 34 is attached to the interior of the sheath 12 through the flexible diaphragm 12. As the pressure of the fluid acts on the enlarged section 34, the optical fiber 16 will be elongated, straining the fiber-grating-based sensor 18*a* and modulating the characteristic light spectrum reflected. The amount of elongation or the pressure sensitivity can be controlled by choosing the ratio of diameters of the enlarged section 34 and that of the optical fiber 16. An 60 μm optical fiber with a 300 μm diameter enlargement will give a wavelength shift of about 330 pm for 1 MPa pressure change.

Figure 8B:
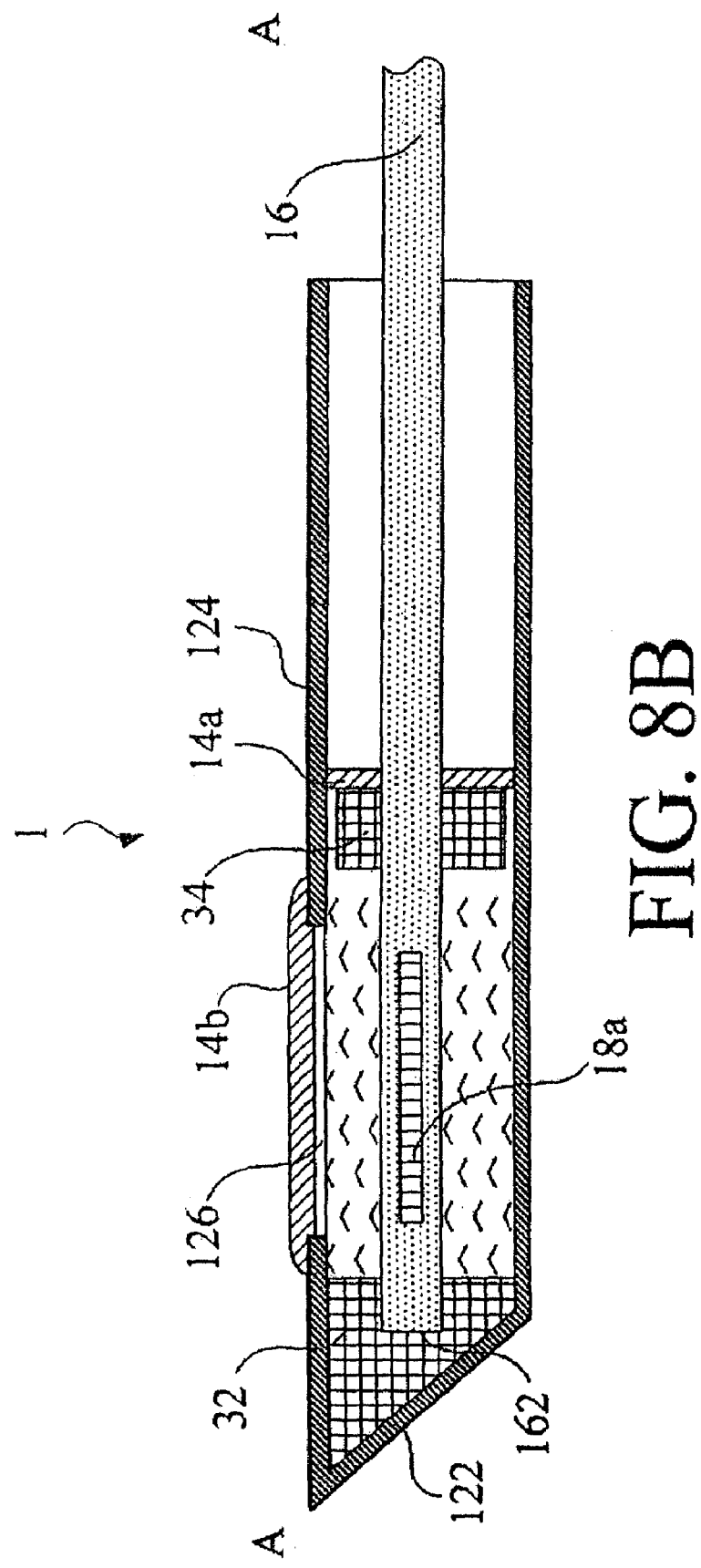
FIG. 8B shows a modification of the embodiment of FIG. 8A wherein the opening is sealed with an additional diaphragm.

FIG. 8B shows a modification of the embodiment of FIG. 8A, wherein the opening 126 is sealed with another flexible diaphragm 14*b* to form a closed space in the sheath 12 between the sheath downstream and upstream. The closed space is previously filled with a fluid. Since the diaphragm 14*b* and the fluid inside the sheath 12 are flexible, thus they will still respond to pressure fluctuation outside the sheath 12.

To sum up, the description of the above-mentioned preferred embodiments is for providing a better understanding on the strengths and spirits of this present invention, not for limiting the domain of the invention. Moreover, it aims to include various modification and arrangement parallel in form into the domain of the patent applied by this present invention. Due to the above mentioned, the domain of the patent applied by the invention should be explained in a macro view to cover all kinds of possible modification and arrangement of equal form.

What is claimed is:

1. A fiber-optic sensing system for measuring a first physical parameter, comprising:
    a sheath having a sealed tip, a main body and a formed-through opening formed on the main body and sealed with a flexible diaphragm;
    an optical fiber thereon comprising a first fiber-grating-based sensor, the optical fiber with the first fiber-grating-based sensor being inserted into an interior of the sheath and only one side of the optical fiber being fixed onto the main body, a segment of the optical fiber encompassing the first fiber-grating-based sensor being underneath the diaphragm;
    an optical device for emitting a sensing light signal into a head end of the optical fiber and receiving a first reflected light signal resulting from the sensing light signal reflected by the first fiber-grating-based sensor, and wherein when the sheath is inserted into a region where the first physical parameter needs to be measured, the region bring, through the diaphragm, a bending strain to the first fiber-grating sensor to induce a variation on the first reflected light signal; and
    a signal processing device, coupled to the optical device, for interpreting the variation on the first reflected light signal into the first physical parameter.

2. The fiber-optic sensing system of claim 1, wherein the first fiber-grating-based sensor is one selected from the group consisting of a fiber Bragg grating, a long period fiber grating and a surface corrugated long period fiber grating, and when the first fiber-grating-based sensor is the long period fiber grating or the surface corrugated long period fiber grating, a mirror coating is plated at a distal end of the optical fiber.

3. The fiber-optic sensing system of claim 2, wherein the optical fiber thereon also comprises a second fiber-grating-based sensor, the optical device also functions receiving a second reflected light signal resulting from the sensing light signal reflected by the second fiber-grating-based sensor, the second fiber-grating-based sensor is disposed in a situation isolated from the region such that the first physical parameter, shielded by the sheath, do not affect the second fiber-grating-based sensor, but a second physical parameter, not shielded by the sheath, still affects the second fiber-grating-sensor and induces a drift on the second reflected light signal, and the signal processing device also functions interpreting the drift on the second reflected light signal into the second physical parameter.

4. The fiber-optic sensing system of claim 3, wherein the second physical parameter that is not shielded by the sheath is a temperature.

5. The fiber-optic sensing system of claim 4, wherein the second fiber-grating-based sensor is identical to the first fiber-grating-based sensor, the drift on the second reflected light signal is used as a drift correction of the temperature for the first reflected light signal.

6. The fiber-optic sensing system of claim 5, wherein the first physical parameter, shielded by the sheath, is a pressure.

7. The fiber-optic sensing system of claim 1, wherein the first fiber-grating -based sensor is relocated to be further away from the diaphragm, to further increase the bending strain on the first fiber-grating-based sensor brought by the region.

8. The fiber-optic sensing system of claim 1, wherein at least one notch is formed on a portion of the segment fixed underneath the diaphragm, away from the diaphragm, to further increase the bending strain on the first fiber-grating-based sensor brought by the region.

9. The fiber-optic sensing system of claim 1, wherein a low stiffness material is previously introduced between the diaphragm and the segment of the optical fiber to further increase the bending strain on the first fiber-grating-based sensor brought by the region.

10. A fiber-optic sensing system for measuring a first physical parameter at N sites, wherein N is a natural number, said system comprising:
    a sheath having a sealed tip, a main body and N formed-through openings formed on the main body, each opening corresponding to one of the N sites and being sealed with a respective flexible diaphragm;
    M1 fiber-grating-based sensors formed on M2 optical fibers inserted into an interior of the sheath and only one side of each of M2 optical fibers being fixed onto the main body, each of N fiber-grating-based sensors of said M1 fiber-grating-based sensors being underneath one of the N diaphragms, wherein Ml is a positive integer larger than or equal to N, and the M2 is a positive integer less than or equal to M1;
    an optical device for emitting a sensing light signal into a head end of each optical fiber and receiving N first reflected light signals resulting from the sensing light signal respectively reflected by said N fiber-grating-based sensors underneath the N diaphragms, and wherein when the sheath is inserted into a region where the first physical parameter needs to be measured, the region bring a respective bending strain to each of the N first fiber-grating sensors underneath the N diaphragms through the corresponding diaphragm to induce a respective variation on the first reflected light signal relative to said one fiber-grating-based sensor; and
    a signal processing device, coupled to the optical device, for respectively interpreting the variations on the N first reflected light signals the into the first physical parameter at the N sites.

11. The fiber-optic sensing system of claim 10, wherein each of the Ml fiber-grating-based sensors is one selected from the group consisting of a fiber Bragg grating, a long period fiber grating and a surface corrugated long period fiber grating, and when said one fiber-grating-based sensor is the long period fiber grating or the surface corrugated long period fiber grating, a respective mirror coating is plated at a distal end of the optical fiber on which said one fiber-grating-based sensor is formed.

12. The fiber-optic sensing system of claim 11, wherein M3 fiber-grating-based sensors of the M1 fiber-grating-based sensors are disposed in M3 situations isolated from the region such that the first physical parameter, shielded by the sheath, do not affect said M3 fiber-grating-based sensors isolated from the region, but a second physical parameter, not shielded by the sheath, still affects said M3 fiber-grating-sensors, the optical device also functions receiving M3 second reflected light signals resulting from the sensing light signal respectively reflected by said M3 fiber-grating-based sensors isolated from the of the region, the second physical parameter induces a drift on each of the second reflected light signals, the signal processing device also functions for respectively interpreting the drifts on the M3 second reflected light signals the into the second physical parameter at the M3 situations.

13. The fiber-optic sensing system of claim 12, wherein the second physical parameter is a temperature.

14. The fiber-optic sensing system of claim 13, wherein at least one of the drifts on the second reflected light signals is used as a drift correction of the temperature for the first reflected light signals.

15. The fiber-optic sensing system of claim 14, wherein the first physical parameter is a pressure.

* * * * *